US00PP37535P2

(12) United States Plant Patent
Hansen

(10) Patent No.: US PP37,535 P2
(45) Date of Patent: Jul. 21, 2026

(54) ***VERNONIA* PLANT NAMED 'Buzz Stop'**

(50) Latin Name: ***Veronia* hybrid**
Varietal Denomination: Buzz Stop

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,949

(22) Filed: Dec. 2, 2025

(51) Int. Cl.
*A01H 6/14* (2018.01)
*A01H 5/02* (2018.01)

(52) U.S. Cl.
USPC ..... Plt./226

(58) Field of Classification Search
USPC ..... Plt./226, 263.1
CPC ..... A01H 6/14; A01H 5/02
See application file for complete search history.

*Primary Examiner* — Keith O. Robinson

(57) ABSTRACT

A new and distinct cultivar of *Vernonia* plant named 'Buzz Stop' with a sturdy full mound habit, linear foliage of dark olive-green with a purplish blush early in the season, numerous inflorescences, on heavily-branched stems, containing rosy-purple disk florets beginning in late summer and continuing for about six weeks. The new plant is attractive to pollinators and useful for landscaping, as a specimen or en masse.

2 Drawing Sheets

Botanical designation: *Vernonia* hybrid.
Cultivar denomination: 'Buzz Stop'.

STATEMENT REGARDING PRIOR DISCLOSURES UNDER 37 CFR 1.77 (b) (6)

The first offer for sale of the new claimed plant was made by Walters Gardens, Inc. to Plant Delights Nursery, Inc. on Dec. 3, 2024. Walters Gardens, Inc. obtained the plant and all information relating thereto, from the inventor. No plants of *Vernonia* 'Buzz Stop' have been sold in this country or anywhere in the world, nor has any disclosure of the new plant been made more than one year prior the filing date of this application, and such sale or disclosure within one year was either derived directly or indirectly from the inventor.

BACKGROUND OF THE PLANT

The present invention relates to the new and distinct cultivar of Ironweed plant herein referred to as *Vernonia* 'Buzz Stop', by the cultivar name 'Buzz Stop', or as the new plant. The new plant represents a new herbaceous perennial grown for landscape use. 'Buzz Stop' was selected by the inventor as a single seedling resulting from a cross at a wholesale perennial nursery in Zeeland, Michigan between 'Southern Cross' (not patented) and 'Plum Peachy' (not patented) on Sep. 26, 2017. The seeds from this cross were collected in the fall of 2017. The single unique seedling was then isolated and compared in subsequent years to other *Vernonia* and found to be different from all cultivars known to the discoverer and eventually given the breeder code 17-14-21.

Asexual propagation at the same nursery in Zeeland, MI, USA by shoot tip cuttings since January of 2021 has shown 'Buzz Stop' to be stable and reproduce true to type in successive generations.

SUMMARY OF THE PLANT

*Vernonia* 'Buzz Stop' has not been observed in all possible environmental conditions. The phenotype may vary slightly with changes in environments such as light intensity, fertility, water availability, etc. without, however, any variation in genotype.

*Vernonia* 'Buzz Stop' is distinct from all cultivars known to the inventor in the following traits:

1. Sturdy full mound of about 113 cm tall and 155 cm wide;
2. Linear foliage of dark olive-green with a purplish blush on young leaves early in the season, and resistant to powdery mildew;
3. Heavily-branched peduncles with densely-packed inflorescences covering the top half of the plant;
4. Inflorescences of dark rosy-purple disk florets;
5. Long flowering period beginning late summer and continuing for about six weeks.

The most similar cultivars known to the inventor: 'Prairie Princess' U.S. Plant Pat. No. 36,918, 'Southern Cross' (not patented), 'Summer's End' U.S. Plant Pat. No. 33,602, 'Summer's Surrender' U.S. Plant Pat. No. 28,475, and 'Summer's Swan Song' U.S. Plant Pat. No. 28,556.

'Prairie Princess' develops a shorter mounded habit with less purplish color on the foliage. 'Southern Cross' is slightly smaller in habit, the young foliage that does not display a purplish tint in high light, and seed production is less prolific. 'Summer's End' has a narrower habit, the leaves are narrower, and the young foliage does not display a purplish tint. 'Summer's Surrender' is significantly taller and wider in habit, and the foliage is narrower without developing a purplish tint. 'Summer's Swan Song' is shorter in habit, the foliage is narrower and does not display a purplish tint.

The female parent is slightly smaller in habit, the young foliage that does not display a purplish tint in high light, and seed production is less prolific. The male parent plant has a taller habit, the young foliage has a purplish tint, the foliage is broader, and the inflorescences are a lighter reddish purple.

BRIEF DESCRIPTION OF THE DRAWINGS

The color drawings illustrate the overall characteristics of *Vernonia* 'Buzz Stop' as a five-year-old plant in a full-sun trial garden in Zeeland, Michigan. The colors are as true as reasonably possible given the technology available. The color values may vary slightly depending on light intensity and quality.

DETAILED BOTANICAL DESCRIPTION

Figure 1:
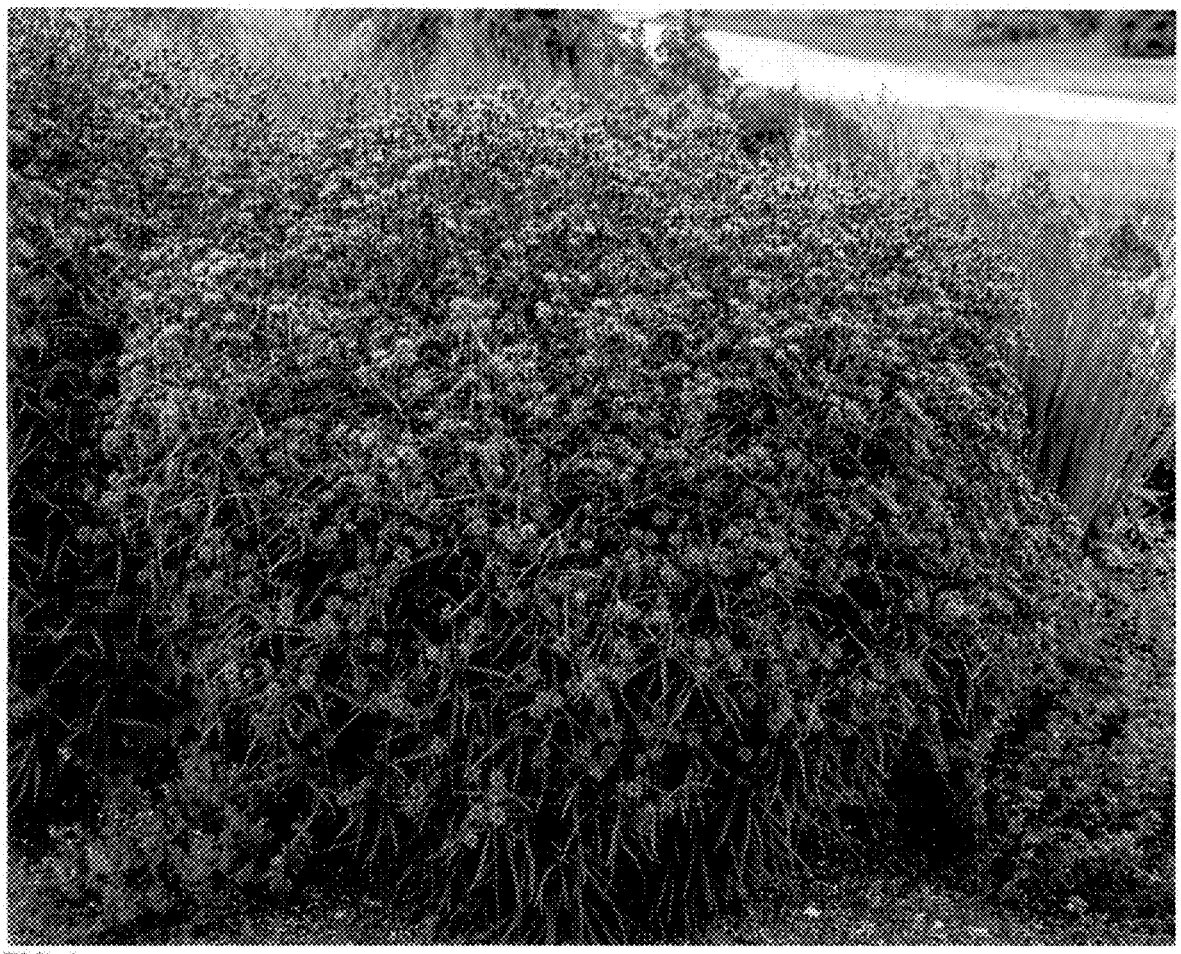
FIG. 1 shows the new plant in a full-sun trial garden.
Figure 2:
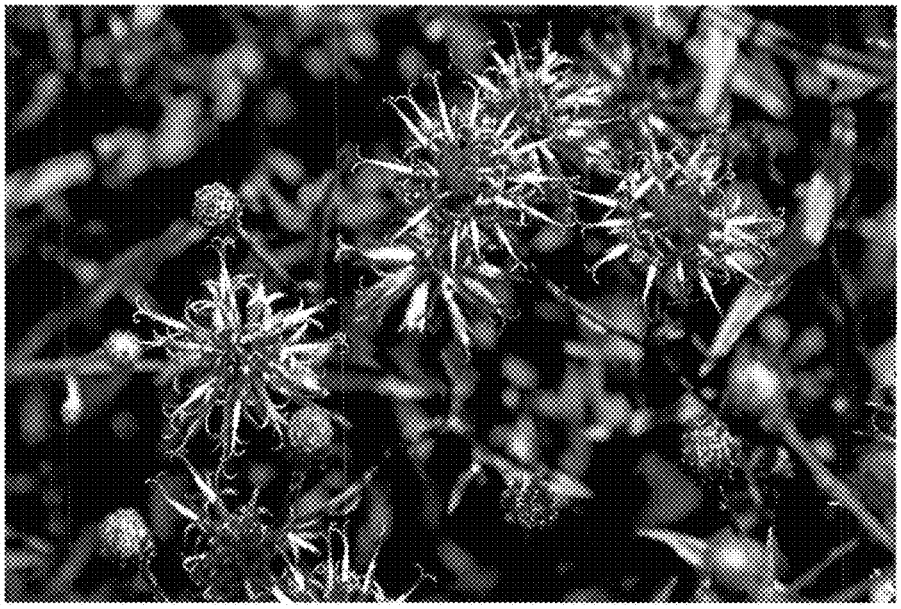
FIG. 2 shows a close-up of the inflorescences and buds of the new plant.
Figure 3:
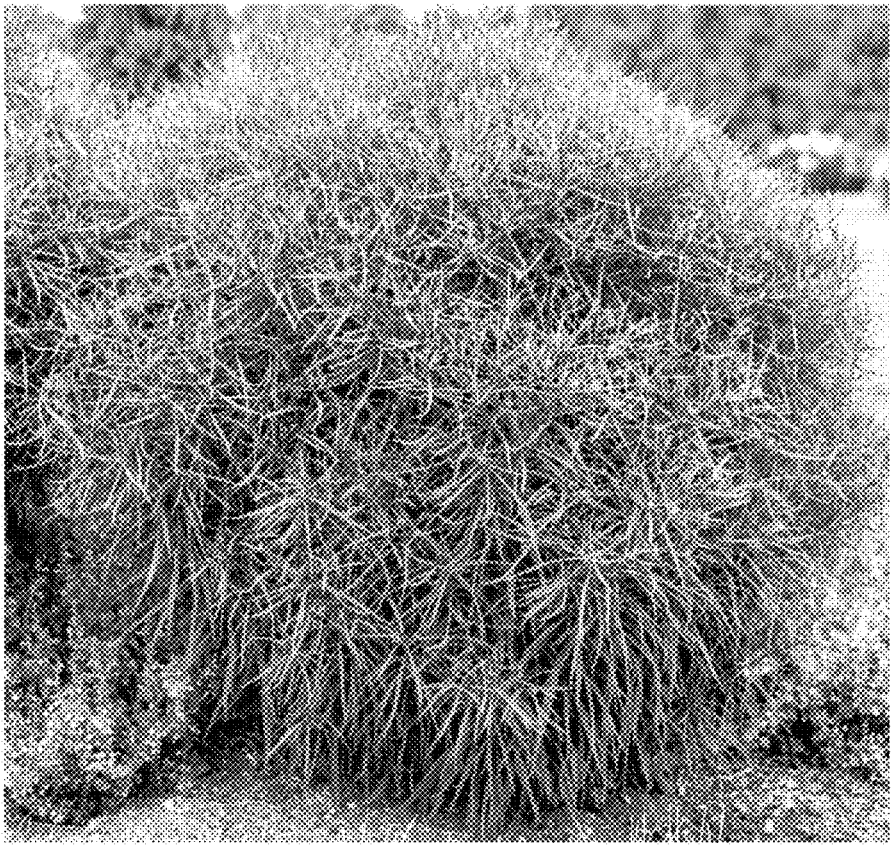
FIG. 3 shows the foliage and habit of the plant before flowering.

The following description of the new plant is based on a five-year-old plant growing in a full-sun trial field in Zeeland, MI, USA. Except for ordinary dictionary color usage, color references are according to The Royal Horticultural Society Colour Chart, 2015 edition.

Parentage: Female or seed parent is 'Southern Cross'; male or pollen parent is 'Plum Peachy';

Asexual propagation: Apical shoot tip cuttings, about 3 to 4 weeks to initiate roots; time to finish as #1 field grown size about 6 months;

Roots: Fibrous; heavily branched; color of older roots near RHS 199C depending on soil matrix, and young active roots near RHS NN155B;

Plant habit: Herbaceous, winter-hardy, rhizomatous, perennial mound with stiff upright stems; to about 113 cm tall and 155 cm wide;

Growth rate: Moderately vigorous;

Leaves: Alternate; simple; linear; acute apex; base attenuate; denticulate with teeth 2 to 4 mm apart; adaxial and abaxial glabrous and matte;

Leaf quantity: About 40 per stem below branched peduncle;

Leaf size: To about 11 cm long and about 8 mm wide;

Leaf color: Young expanding leaves adaxial nearest RHS 187A and abaxial distally between RHS 187A and RHS N79A; mature adaxial nearest RHS NN137A and abaxial nearest RHS NN137B;

Foliar fragrance: None noted;

Veins: Pinnate; glabrous adaxial and abaxial;

Vein color: Adaxial midrib, primary, and secondary veins nearest RHS 146B; abaxial midrib and primary and secondary veins nearest RHS 146B;

Petiole: Leaves sessile;

Stems: Upright; cylindrical with longitudinal ridges and furrows; micro-puberulent; stiff; heavily branched; surface matte; about 73 per plant;

Internodes: About 40 per plant below flower branches; internode spacing about 1.1 cm;

Stem size: Main stem to about 88 cm tall and 0.8 cm diameter, with upper branches extending above the main stem about 2 mm diameter and about 20 cm long;

Stem color: Proximal portion and regions protected from high sun exposure between RHS 146B and RHS 146C, distal portions in high sun exposure nearest RHS 183B; and nodes between RHS 202A and RHS 183B;

Branches: Cylindrical; micro-puberulent; up to 21 per main stem in upper 32 to 54 cm of peduncle; to about 28 cm long and 0.3 cm diameter;

Branch color: Between RHS N186C and RHS N186B;

Peduncle: Cylindrical; micro-puberulent; strong; longitudinally furrowed; upright; to about 6mm long and 1 mm diameter; color between RHS N186C and RHS N186B;

Pedicel: Of individual disk flowers too small to measure or observe color;

Inflorescence: Capitula organized as compound corymbiform; composite consisting of about 30 disk florets per capitulum and no ray florets; on heavily branched terminal stems; individual inflorescence about 21 mm diameter, about 17 mm tall from bottom of involucral bracts to top of exerted style; attitude upright in center and outwardly toward exterior;

Receptacle: About 5 mm tall and 4 mm across; color nearest RHS 148C;

Inflorescence fragrance: None detected;

Phyllaries: About 50 per capitulum in about 4 or 5 whorls; deltoid to lanceolate; long narrowly acute apex; truncate base; margin entire; glabrous; to about 5 mm long and 1.5 mm across near middle, increasing in size distally; divergent, not adpressed distally;

Phyllary color: Adaxial and abaxial between RHS 143A and RHS 143B proximally, middle portion nearest RHS 187C and apex nearest RHS 187A;

Flowering period: Beginning late summer for about six weeks; individual florets effective for about 5 to 7 days;

Inflorescence longevity: 6 to 8 days;

Inflorescence buds with disk florets unopen and upright: Cylindrical; to about 11 mm tall and 7 mm across near apex of tepals;

Floret buds: Oblong; with tepals still erect 9 mm tall and 1.5 mm across;

Floret bud color: Disk florets while still upright exposed abaxial corolla color between RHS 77A and RHS N81A;

Disk florets: Imperfect; complete; typically about 30 per inflorescence; about 15 mm long and 6 mm across distally and basal corolla tube about 1.5 mm across;

*Corolla tube.*—Consisting of five linear tepals; about 11 mm long, flared in the distal 3 mm and 6 mm across at apices.

*Tepals.*—Five; apex acute; margin entire; glabrous and slightly lustrous adaxial and abaxial; connate in the proximal 8 mm; to about 12 mm long and about 0.5 mm wide at fusion.

*Tepal color.*—Adaxial and abaxial proximal 1 mm nearest RHS NN155D, adaxial and abaxial distally nearest RHS N81A when first opening, lightening to between RHS N82A and RHS N82B.

*Pistil.*—Single; to about 15 mm long.

*Style.*—Single; cylindrical; about 11.5 mm long and about 0.2 mm diameter; distally enclosed in anther column; color proximal two-thirds nearest RHS NN155D, distal one-third nearest RHS N81A.

*Stigma.*—Bifid, cylindrical; about 1 mm long and 0.1 mm diameter; color between RHS 77A and RHS 79B.

*Ovary.*—Elliptical; about 3 mm long and 1 mm diameter; color nearest RHS 75D.

*Stamen.*—5; connate around the style.

*Filament.*—5; cylindrical; thin; about 5 mm long and 0.1 mm diameter; color nearest RHS NN155D.

*Anther.*—longitudinal; introrse; individually oblong; to about 4 mm long and about 1 mm across; color between RHS 195A and RHS N187C.

*Pollen.*—Moderate; color nearest RHS N187D.

*Pappus.*—about 25; straight; thin; about 5 mm long and less than 0.1 mm diameter. color nearest RHS 79A.

Seed: Achene; conical; about 4 mm long and 0.5 mm wide; apex truncate; base acute; color nearest RHS 199B;

*Vernonia* 'Buzz Stop' is resistant to powdery mildew (*Golovinomices* sp.) and maintains most of the lower foliage through the season. No susceptibility and resistance of other diseases and pest that are common to other Ironweed cultivars has been observed.

The new plant is winter hardy and grows well in USDA zones 4 through 9 and resists lodging from heavy rains.

I claim:

1. A new and distinct cultivar of *Vernonia* plant named 'Buzz Stop' as herein described and illustrated.

* * * * *